US009056824B2

(12) United States Patent
Hampton, Jr. et al.

(10) Patent No.: US 9,056,824 B2
(45) Date of Patent: *Jun. 16, 2015

(54) PREPARATION OF HYDROXY ALDEHYDES

(71) Applicant: Eastman Chemical Company, Kingsport, TN (US)

(72) Inventors: Kenneth Wayne Hampton, Jr., Glimer, TX (US); Eugene H. Brown, Gilmer, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/755,879

(22) Filed: Jan. 31, 2013

(65) Prior Publication Data

US 2014/0213827 A1    Jul. 31, 2014

(51) Int. Cl.
*C07C 45/72* (2006.01)
*C07C 45/75* (2006.01)
*C07C 45/85* (2006.01)

(52) U.S. Cl.
CPC ............... *C07C 45/75* (2013.01); *C07C 45/85* (2013.01)

(58) Field of Classification Search
CPC .......... C07C 45/72; C07C 45/74; C07C 45/75
USPC ................................................. 568/463, 464
See application file for complete search history.

(56) References Cited

U.S. PATENT DOCUMENTS

| 3,808,280 | A |   | 4/1974  | Merger et al. |
|-----------|---|---|---------|---------------|
| 3,876,706 | A |   | 4/1975  | Levanevsky et al. |
| 3,886,219 | A |   | 5/1975  | Reich |
| 3,935,274 | A |   | 1/1976  | Jacobsen et al. |
| 3,939,216 | A |   | 2/1976  | Wright |
| 3,975,450 | A |   | 8/1976  | Palmer et al. |
| 4,036,888 | A |   | 7/1977  | Couderc et al. |
| 4,215,076 | A |   | 7/1980  | Stueben et al. |
| 4,250,337 | A |   | 2/1981  | zur Hausen et al. |
| 4,386,219 | A |   | 5/1983  | Merger et al. |
| 4,393,251 | A |   | 7/1983  | Broecker et al. |
| 4,665,219 | A |   | 5/1987  | Merger et al. |
| 4,851,592 | A |   | 7/1989  | Morris |
| 4,855,515 | A | * | 8/1989  | Morris et al. ............... 568/862 |
| 4,918,247 | A |   | 4/1990  | Breitkopf et al. |
| 4,933,473 | A |   | 6/1990  | Ninomiya et al. |
| 5,072,058 | A |   | 12/1991 | Dämbkes et al. |
| 5,093,537 | A |   | 3/1992  | Unruh et al. |
| 5,144,088 | A |   | 9/1992  | Salek et al. |
| 5,146,012 | A |   | 9/1992  | Salek et al. |
| 5,166,370 | A |   | 11/1992 | Liotta, Jr. et al. |
| 5,185,478 | A |   | 2/1993  | Salek et al. |
| 5,334,778 | A |   | 8/1994  | Haas et al. |
| 5,380,919 | A |   | 1/1995  | Merger et al. |
| 5,395,989 | A | * | 3/1995  | Yoneoka et al. ............... 568/862 |
| 5,532,417 | A |   | 7/1996  | Salek et al. |
| 5,608,121 | A |   | 3/1997  | Ninomiya et al. |
| 5,841,002 | A |   | 11/1998 | Harrison et al. |
| 5,888,923 | A |   | 3/1999  | Chen et al. |
| 6,018,074 | A |   | 1/2000  | Kratz et al. |
| 6,077,980 | A |   | 6/2000  | Ninomiya et al. |
| 6,080,896 | A |   | 6/2000  | Ninomiya et al. |
| 6,096,931 | A |   | 8/2000  | Frohning et al. |
| 6,187,971 | B1 |  | 2/2001  | Kratz et al. |
| 6,201,159 | B1 |  | 3/2001  | Choi et al. |
| 6,255,541 | B1 |  | 7/2001  | Paatero et al. |
| 6,268,539 | B1 | * | 7/2001 | Sen-Huang et al. ........... 568/853 |
| 6,340,778 | B1 |  | 1/2002  | Bueschken et al. |
| 6,545,189 | B1 | * | 4/2003 | Nousiainen .................. 568/862 |
| 6,552,232 | B2 |  | 4/2003  | Mehnert et al. |
| 6,586,641 | B2 |  | 7/2003  | Dernbach et al. |
| 6,593,502 | B2 |  | 7/2003  | Salmi et al. |
| 6,600,078 | B1 |  | 7/2003  | Mahmud et al. |
| 6,914,164 | B2 |  | 7/2005  | Koch et al. |
| 7,060,861 | B2 |  | 6/2006  | Dernbach et al. |
| 7,087,800 | B2 |  | 8/2006  | Ninomiya et al. |
| 7,301,058 | B2 |  | 11/2007 | Wartini et al. |
| 7,368,612 | B2 |  | 5/2008  | Amemiya et al. |
| 7,388,116 | B2 |  | 6/2008  | Maas et al. |
| 7,439,406 | B2 |  | 10/2008 | Wartini et al. |
| 7,462,747 | B2 |  | 12/2008 | Sirch et al. |
| 7,767,865 | B2 |  | 8/2010  | Sirch et al. |
| 8,013,192 | B2 |  | 9/2011  | Husen et al. |
| 2002/0007095 | A1 | | 1/2002 | Ninomiya et al. |
| 2003/0009062 | A1 | | 1/2003 | Dobert et al. |
| 2008/0004475 | A1 | | 1/2008 | Sirch et al. |

(Continued)

FOREIGN PATENT DOCUMENTS

DE        10317545 A1      11/2004
JP        61-018747        1/1986

(Continued)

OTHER PUBLICATIONS

"Synthesis of Neopentyl Glycol"; posted Jul. 13, 2010 by China Papers, retrieved on Aug. 31, 2012 from http://mt.china-papers.com/? p=112613, 1 page.

Gutsche, C. David et al,; "Tertiary Amine Catalysis of the Adol Condensation": J. Am, Chem, Soc., vol. 84(149); 1962, pp. 3775-3777.

Hashmi, Azhar; "Cross-Aldol Condensation of Isobutyraldehyde and Formaldehyde Using Phase Transfer Catalyst"; Journal of Saudi Chemical Society; 2013; http://dx.doi.org/10.1016/j.jscs.2012.12. 012.

(Continued)

*Primary Examiner* — Sikarl Witherspoon

(74) *Attorney, Agent, or Firm* — William K. McGreevey

(57) ABSTRACT

An improved process for preparing hydroxy aldehydes, such as hydroxypivaldehyde, is provided. Specifically, the process employs an alkaline additive for separating by-product amine salts from a hydroxy aldehyde and other reaction products formed in the process of preparing a hydroxy aldehyde using an amine catalyst.

56 Claims, 1 Drawing Sheet

(56) References Cited

U.S. PATENT DOCUMENTS

| | | |
|---|---|---|
| 2009/0069004 A1 | 3/2009 | Ergen et al. |
| 2010/0113836 A1 | 5/2010 | Sirch et al. |
| 2011/0098515 A1 | 4/2011 | Schalapski et al. |
| 2011/0184212 A1 | 7/2011 | Schulz et al. |
| 2011/0272270 A1 | 11/2011 | Schlitter et al. |
| 2011/0282106 A1 | 11/2011 | Steiniger et al. |
| 2011/0313203 A1 | 12/2011 | Sirch et al. |
| 2011/0313204 A1 | 12/2011 | Zim et al. |
| 2012/0004472 A1 | 1/2012 | Sirch et al. |

FOREIGN PATENT DOCUMENTS

| | | |
|---|---|---|
| JP | 4074143 A | 3/1992 |
| KR | 10-0584707 B1 | 5/2006 |
| KR | 100584707 | 5/2006 |
| KR | 10-0636869 B1 | 10/2006 |
| KR | 100636869 | 10/2006 |
| WO | 00/58246 A1 | 10/2000 |
| WO | 00/58247 A1 | 10/2000 |

OTHER PUBLICATIONS

Notification of Transmittal of the International Search Report and the Written Opinion of the International Searching Authority, or the Declaration date of mailing May 28, 2014 received in International Patent Application No. PCT/US2014/012025.

Notification of Transmittal of the International Search Report and the Written Opinion of the International Searching Authority, or the Declaration date of mailing Apr. 29, 2014 received in International Patent Application No. PCT/US2014/012032.

Co-pending U.S. Appl. No. 13/755,910, filed Jan. 31, 2013; Hampton, Jr. et al.; now U.S. Patent No. 8,710,278.

* cited by examiner

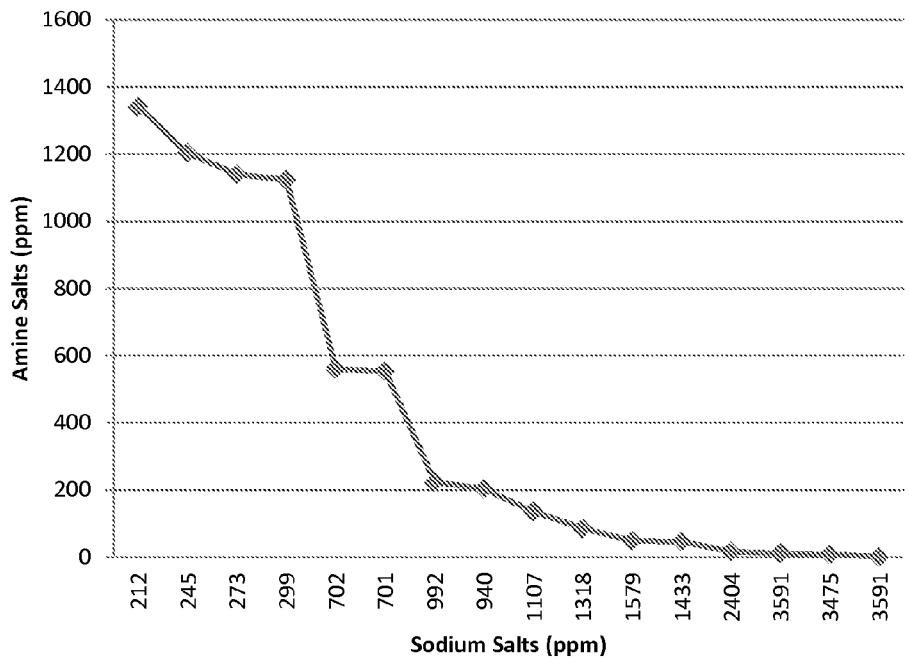

PREPARATION OF HYDROXY ALDEHYDES

BACKGROUND

Hydroxypivaldehyde (HPA, 3-hydroxy-2,2-dimethylpropanal) is widely used as a starting material for the preparation of various useful products such as neopentyl glycol (NPG, 2,2-dimethyl-1,3-propanediol), ester glycol (HPHP, Hydroxypivalyl Hydroxypivalate), and spiroglycol [SPG, 3,9-bis(1, 1-dimethyl-2-hydroxyethyl)-2,4,8,10-tetraoxaspiro(5.5)undecane], which are used in lubricants, plastics, surface coatings, surfactants, and synthetic resins. HPA is typically produced by an Aldol condensation of isobutyraldehyde (iHBu) and formaldehyde (HCHO) in the presence of an amine catalyst to form HPA, as depicted in the following Scheme 1:

Scheme 1

Preparation of Hydroxypivaldehyde in an Aldol Condensation

Scheme 1 Preparation of Hydroxypivaldehyde in an Aldol Condensation

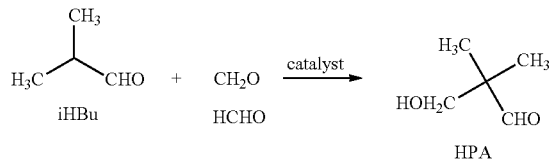

The tertiary amine catalyst systems are usually run with an excessive amount of aldehyde, which enables the reaction to be carried out in a homogeneous reaction mixture. In these processes, the selectivity of Aldol is increased when compared to the alkaline catalyst systems. However, the use of tertiary amine catalysts in Aldol condensations has a problem in that the tertiary amine catalyst reacts with organic acids to form salts. The organic acids are either from the formaldehyde raw material in the form of formic acid or generated via Cannizaaro reaction of aldehydes during the condensation process. These amine salts cannot be separated from the HPA by distillation and are carried on into the hydrogenation reaction. The amine salts deactivate the metal catalyst used in the hydrogenation reaction. In addition, they decompose the Aldol condensation product during the distillation of product at high temperatures. Thus, overall yields are dramatically decreased.

SUMMARY

This invention provides simplified processes of preparing hydroxy aldehydes produced via the Aldol condensation reaction of formaldehyde with another aldehyde. Additional details of example methods are further described below in the Detailed Description. This summary is not intended to identify essential features of the claimed subject matter, nor is it intended for use alone in determining the scope of the claimed subject matter.

According to an embodiment, the present invention describes a process for the preparation of hydroxy aldehyde comprising:

contacting formaldehyde and another aldehyde in the presence of an amine catalyst under Aldol condensation conditions to produce a stream comprising hydroxy aldehyde and amine salts;

contacting the stream with an alkaline additive to form a mixture; and purifying the mixture to remove the amine salts.

Another embodiment provides a method of producing a polyol comprising:

contacting formaldehyde and another aldehyde in the presence of an amine catalyst under Aldol conditions to produce a stream comprising hydroxy aldehyde and amine salts;

contacting the stream with an alkaline additive to form a mixture;

purifying the mixture to remove the amine salts to form a purified hydroxy aldehyde stream; and hydrogenating the purified hydroxy aldehyde stream to form a polyol.

Yet another embodiment describes a process for the preparation of hydroxypivaldehyde comprising:

contacting formaldehyde and isobutyraldehyde in the presence of an amine catalyst under Aldol condensation conditions to produce a stream comprising hydroxypivaldehyde and amine salts;

contacting the stream with an alkaline additive to form a mixture; and purifying the mixture to remove the amine salts.

BRIEF DESCRIPTION OF THE DRAWING

FIG. 1 shows the effect of caustic addition on the removal of amine salts in the hydrogenation feed.

DETAILED DESCRIPTION

According to an embodiment, the invention describes a process for removing or minimizing the presence of nitrogen-containing salts (amine salts) in the product stream of an Aldol reaction prior to purification (e.g. via distillation or evaporation) of the product stream and subsequent hydrogenation to a polyol. For example, an embodiment concerns the removal of or minimization of amine salts from a hydroxy aldehyde (such as, for example, HPA) containing stream before producing a polyol (such as, for example, NPG) by hydrogenation.

According to an embodiment, the invention describes a process for the preparation of a hydroxy aldehyde. The process can include contacting formaldehyde and another aldehyde in the presence of an amine catalyst under Aldol condensation conditions to produce a stream comprising a hydroxy aldehyde and amine salts and contacting the stream with an alkaline additive to form a mixture.

The mixture may be purified before hydrogenation by any means or process that removes low boilers (e.g. unreacted products and amine salts, that boil-off with water) such as by distillation or evaporation. For example, the mixture may be purified by distillation (e.g. on a low boiler removal column), wherein distillation is carried out on the obtained hydroxy aldehyde and amine salt stream. The hydroxy aldehyde is freed from water, unreacted products, and the amine salts by distillation at appropriate combinations of temperature and pressure. Typical conditions may be, for example, a temperature of from about 80° C. to about 135° C.; or from about 85° C. to about 120° C.; or from about 90° C. to about 115° C. Moreover, the distillation pressure can be from about 0 mm to about 1000 mm; or from about 100 mm to about 500 mm; or from about 220 mm to about 300 mm; or even at about 250 mm.

According to an embodiment, the hydroxy aldehyde and amine salts comprising stream and an alkaline additive ("additive") are combined to form a mixture prior to purification. The amount of additive that is added for removing amine salts while not catalyzing retro Aldol of the hydroxy aldehyde to the starting formaldehyde and another aldehyde in the hydroxy aldehyde and amine salts comprising stream prior to purification can be determined by analysis of the hydroxy aldehyde and amine salts comprising stream. For example, the amount of alkaline additive supplied to the hydroxy aldehyde and amine salts comprising stream may be selected by the analysis of the hydroxy aldehyde stream and amine salts comprising (e.g. the hydrogenation feed) prior to purification.

The concentration of the amine salts can depend on the Aldol reactor variables and raw materials used. Moreover, the salts are a result of acids present in the reaction mixture. The amine catalyst reacts with acids to form salts of formates, isobutyrates, and hydroxypivalates. Typically the concentration of the amine salts can be from about 3000 to about 1000 ppm. Moreover, the additive breaks up these amine salts during purification (e.g. in the distillation column) to liberate the amine to be recovered in the low boiler stream. According to an embodiment, about 50 ppm to about 5000 ppm; about 500 ppm to about 3000 ppm; or even about 1000 ppm to about 2000 ppm of alkaline additive is added with the hydroxy aldehyde and amine salts comprising stream during purification (e.g. to a distillation column such as a low boiler removal column). Alternatively, the additive is added at a weight percent excess when compared to the weight percent of the amine salt. For example, after a weight percent of the amine salts is determined, the additive can be added at a less than 10 weight percent excess, or a less than 5.0 weight percent excess, or a less than 1.0 weight percent excess when compared to the previously determined weight percent of the amine salts.

By way of example, determining the amount of alkaline additive to add to the hydroxy aldehyde and amine salts comprising stream may involve measuring sodium and nitrogen after purification (e.g. at the outlet of the distillation column) generally by known techniques. The measurement can be online or by regular sampling. Typical sodium analysis can be accomplished with Inductively Coupled (ICP) optical emissions spectrometer and nitrogen analysis with Total Nitrogen Analyzers (TN-10). Once the amount of sodium and nitrogen has been determined, an amount of alkaline additive can be added to the hydroxy aldehyde and amine salts comprising stream to remove or minimize the concentration of amine salts in the stream prior to hydrogenation. The amount of alkaline additive supplied can be regulated, for example, such that the nitrogen measurement is minimized to a level that is determined by a cost benefit analysis. For example, the additive can be metered in using flow control valves and a metering pump.

According to an embodiment, examples of the another aldehyde include but are not limited to formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, and glutaraldehyde.

According to an embodiment, examples of the hydroxy aldehyde include but are not limited to 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, and HPA.

According to an embodiment, examples of the tertiary amine catalyst include but are not limited to triethylamine, tri-n-propylamine, tri-n-butylamine, trimethlyamine and mixtures thereof. For example, trimethylamine (TMA) can be used due to the low boiling point of TMA compared to the reactants and products. The lower boiling point facilitates distillative or evaporative removal of the amine salts in the column once the inorganic base dissociates from the amine counter ion.

According to an embodiment, the alkaline additive used can be any substance that can achieve dissociation of the amine salt due to the base strength (pKa scale) such as inorganic bases. This can include carbonates, hydrogencarbonates and hydroxides of alkali metals and alkaline earth metals. Specifically, $Na_2CO_3$, $K_2CO_3$, $CaCO_3$, $NaHCO_3$, $KHCO_3$, NaOH, KOH, and $Ca(OH)_2$. Inorganic bases can be used as a solution, preferably as an aqueous solution, for example, in a concentration of about 5% to about 50% by weight.

According to an embodiment, the hydroxy aldehyde is HPA which can be prepared by reacting isobutyraldehyde and formaldehyde in the presence of a tertiary amine catalyst. Moreover, according to an embodiment of the invention, one or more alkaline additive(s) is/are supplied to the HPA and amine salts containing stream prior to purification to establish a hydrogenation feed with little to no amine salts. Alternatively, the HPA, amine salts containing stream, and additive(s) are added together during purification (e.g. to the distillation column).

The combining or contacting of the formaldehyde and another aldehyde in the presence of the catalyst is carried out under Aldol reaction conditions (i.e., those conditions of temperature, pressure, length of contact time, etc.) which enable or allow the reaction to proceed. Included in such conditions are those required to supply or to maintain the aldehyde reactant(s) in the liquid phase (i.e., temperature, pressure) so that intimate contact with the catalyst is realized. Suitable temperatures, for example, may range from about 0° C. to about 200° C.; or from about 20° C. to about 150° C.; or from about 70° C. to about 110° C. Pressures may be varied considerably and may range from about 1 psig to about 300 psig; from about 5 psig to about 100 psig; or from about 10 psig to about 40 psig. For a batch reaction, total reaction times (i.e. the time to completion or substantial completion of the condensation reaction) will vary considerably, but in general will range from about 30 minutes to about 24 hours or from about 30 minutes to about 2 hours. In the case of a continuous process, with continuous feed to a reaction zone and continuous withdrawal of product containing mixture, average contact time may range from about 30 minutes to about 48 hours or from about 30 minutes to about 2 hours, contact time herein being understood as the liquid volume in the reactor divided by the volumetric flow rate of the liquid.

EXAMPLES

The process according to the embodiments described above is further illustrated by, but not limited to, the following examples wherein all percentages given are by weight unless specified otherwise.

Example 1

Continuous Synthesis of Hydroxypivaldehyde (HPA)

The process described herein is for the preparation of HPA. A one gallon reactor equipped with a stirrer was continuously fed with isobutyraldehyde (iHBu), about 50% formaldehyde (HCHO) aqueous solution (methanol content about 0.5%) and 2% TMA solution in isobutyraldehyde. The ratio of isobutyraldehyde/formaldehyde is maintained at 1.1/1 to 1.6/1 by adjusting the feed rates to the Aldol reactor. The reactor was maintained at 70° C. to 110° C. under a nitrogen pressure of 10 to 40 psig. The residence time was adjusted to 1 hour by removing the condensation product mixture containing crude hydroxypivaldehyde at a set rate. This condensation product mixture having the composition shown in Table 1 was introduced continuously to the middle of a multi-staged distillation column. The multi-stage column was maintained at temperatures to remove TMA, iHBu and water overhead and crude hydroxypivaldehyde exiting the overflow where the column bottom temperature was maintained between 80° C. to 100° C. at 5 psig. The overhead is returned to the Aldol reactor as the TMA catalyst feed. The overflow is fed continuously to a trickle-bed hydrogenation reactor.

TABLE 1

|  | Aldol Product (wt %) | Hydrogenation Feed (wt %) |
|---|---|---|
| Water | 20-15 | 20-15 |
| Isobutyraldehyde | 10-8 | 0 |
| Trimethylamine | 2.0-1.9 | 0 |
| Amine salts (ppm) | 2000-1000 | 2000-1000 |
| Sodium Salts (ppm) | 0 | 0 |
| Hydroxypivaldehyde | 70 | 80-75 |
| Others | 5-4 | 5-4 |

Example 2

Caustic Addition to Aldol Product

Hydroxypivaldehyde was prepared as described in Example 1. To reduce or minimize the amine salts, a 6% solution of caustic was metered continuously into the feed (Aldol Product) of the distillation column. The multi-stage column was maintained at temperatures to remove TMA, iHBu and water overhead and crude hydroxypivaldehyde exiting the overflow. The resulting Hydrogenation Feed composition is shown in Table 2 and the relationship between the continuous additions of caustic on the removal of amine salts is shown in FIG. 1.

TABLE 2

|  | Aldol Product (wt %) | Hydrogenation Feed (wt %) |
|---|---|---|
| Water | 20-15 | 20-15 |
| Isobutyraldehyde | 10-8 | 0 |
| Trimethylamine | 2.0-1.9 | 0 |
| Amine salts (ppm) | 2000-1000 | 200-0 |
| Sodium Salts (ppm) | 0 | 3500-1000 |
| Hydroxypivaldehyde | 70 | 80-75 |
| Others | 5-4 | 5-4 |

Example 3

Carbonate Addition to Aldol Product

Hydroxypivaldehyde was prepared as described in Example 1. To reduce or minimize the nitrogen-containing salts, a 3% solution of sodium carbonate was metered continuously into the feed (Aldol Product) of the distillation column. The multi-stage column was maintained at temperatures to remove TMA, iHBu and water overhead and crude hydroxypivaldehyde exiting the overflow. The resulting Hydrogenation Feed composition is shown in Table 3.

TABLE 3

|  | Aldol Product (wt %) | Hydrogenation Feed (wt %) |
|---|---|---|
| Water | 20-15 | 20-15 |
| Isobutyraldehyde | 10-8 | 0 |
| Trimethylamine | 2.0-1.9 | 0 |
| Amine salts (ppm) | 2000-1000 | 200-0 |
| Sodium Salts (ppm) | 0 | 3500-1000 |
| Hydroxypivaldehyde | 70 | 80-75 |
| Others | 5-4 | 5-4 |

Although embodiments have been described in language specific to methodological acts, the embodiments are not necessarily limited to the specific acts described. Rather, the specific acts are disclosed as illustrative forms of implementing the embodiments.

What is claimed is:

1. A process for the preparation of hydroxy aldehyde comprising:
    contacting formaldehyde and another aldehyde in the presence of an amine catalyst under Aldol condensation conditions to produce a stream comprising a hydroxy aldehyde and amine salts;
    contacting the stream with an alkaline additive to form a mixture; and
    purifying the mixture to remove the amine salts.

2. The process according to claim 1, wherein the hydroxy aldehyde comprises 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, or hydroxypivaldehyde.

3. The process according to claim 1, wherein said another aldehyde comprises formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, or glutaraldehyde.

4. The process according to claim 1, wherein the amine catalyst is triethylamine, tri-n-propylamine, tri-n-butylamine, trimethlyamine, or mixtures thereof.

5. The process according to claim 1, wherein the alkaline additive comprises a carbonate, a hydrogen carbonate, or a hydroxide of an alkali metal or alkaline earth metal.

6. The process according to claim 5, wherein the alkaline additive is $Na_2CO_3$, $K_2CO_3$, $CaCO_3$, $NaHCO_3$, $KHCO_3$, NaOH, KOH, $Ca(OH)_2$, or combinations thereof.

7. The process according to claim 1, wherein the purifying is by distillation.

8. A process of producing a polyol comprising:
    contacting formaldehyde and another aldehyde in the presence of an amine catalyst under Aldol condensation conditions to produce a stream comprising a hydroxy aldehyde and amine salts;
    contacting the stream with an alkaline additive to form a mixture;

purifying the mixture to remove the amine salts to form purified hydroxy aldehyde stream; and hydrogenating the purified hydroxy aldehyde stream to form a polyol.

9. The process according to claim 8, wherein the hydroxy aldehyde comprises 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, or hydroxypivaldehyde.

10. The process according to claim 8, wherein said another aldehyde comprises formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, or glutaraldehyde.

11. The process according to claim 8, wherein the amine catalyst is triethylamine, tri-n-propylamine, tri-n-butylamine, trimethlyamine, or mixtures thereof.

12. The process according to claim 8, wherein the alkaline additive comprises a carbonate, a hydrogen carbonate, or a hydroxide of an alkali metal or alkaline earth metal.

13. The process according to claim 12, wherein the alkaline additive is $Na_2CO_3$, $K_2CO_3$, $CaCO_3$, $NaHCO_3$, $KHCO_3$, NaOH, KOH, $Ca(OH)_2$, or combinations thereof.

14. The process according to claim 8, wherein the purifying is by distillation.

15. A process for the preparation of hydroxypivaldehyde comprising:

contacting formaldehyde and isobutyraldehyde in the presence of an amine catalyst under Aldol condensation conditions to produce a stream comprising hydroxypivaldehyde and amine salts;

contacting the stream with an alkaline additive to form a mixture; and purifying the mixture to remove the amine salts.

16. The process according to claim 15, wherein the amine catalyst is triethylamine, tri-n-propylamine, tri-n-butylamine, trimethlyamine, or mixtures thereof.

17. The process according to claim 15, wherein the alkaline additive comprises a carbonate, a hydrogen carbonate, or a hydroxide of an alkali metal or alkaline earth metal.

18. The process according to claim 17, wherein the alkaline additive is $Na_2CO_3$, $K_2CO_3$, $CaCO_3$, $NaHCO_3$, $KHCO_3$, NaOH, KOH, $Ca(OH)_2$, or combinations thereof.

19. The process according to claim 15, wherein the purifying is by distillation.

20. The process according to claim 1, wherein the contacting of formaldehyde and another aldehyde is carried out in a reactor, wherein the stream is removed from the reactor prior to contact with the alkaline additive.

21. The process according to claim 1, wherein the purifying is carried out in a distillation column, wherein the alkaline additive is added into the mixture fed to the distillation column.

22. The process according to claim 1, wherein the purifying is carried out in a distillation column, wherein the alkaline additive is added into the distillation column.

23. The process according to claim 1, wherein the alkaline additive causes dissociation of the amine salts.

24. The process according to claim 1, wherein the alkaline additive is contacted with the stream in an amount that is less than 10 weight percent excess compared to the weight percent of the amine salts.

25. The process according to claim 1, wherein the amine salts are formed by the reaction of the amine catalyst with an organic acid during Aldol condensation.

26. The process according to claim 1, wherein the contacting of formaldehyde and another aldehyde is carried out in a homogeneous reaction mixture.

27. The process according to claim 1, wherein the purifying is by distillation and produces an overhead stream, wherein the contacting of formaldehyde and another aldehyde is carried out in a reactor, wherein at least a portion of said overhead stream is recycled back to the reactor.

28. The process according to claim 27, wherein the overhead stream comprises at least a portion of the amine catalyst.

29. The process according to claim 27, wherein the purifying produces an overflow stream comprising a crude hydroxy aldehyde.

30. The process according to claim 29, wherein the crude hydroxy aldehyde is subsequently subjected to hydrogenation.

31. The process according to claim 1, wherein the another aldehyde is isobutyraldehyde, the amine catalyst is trimethylamine, and the alkaline additive is NaOH.

32. The process according to claim 1, wherein the contacting of formaldehyde and another aldehyde is carried out at a temperature in the range of from about 20° C. to about 150° C., a pressure in the range from about 5 psig to about 100 psig, and a total reaction time in the range of from about 30 minutes to about 2 hours.

33. The process according to claim 1, wherein the purifying of the mixture produces a purified stream, further comprising measuring the sodium and/or nitrogen content of the purified stream, further comprising metering the amount of the alkaline additive contacted with the stream based on the measured sodium and/or nitrogen content of the purified stream.

34. The process according to claim 1, wherein the process is a continuous process.

35. A process comprising:

conducting an Aldol condensation reaction in a reaction zone containing an amine catalyst to thereby produce a reaction mixture comprising a hydroxy aldehyde, wherein one or more amine salts are produced during the Aldol condensation reaction;

purifying at least a portion the reaction mixture in a purification zone to thereby produce a purified product comprising at least a portion of the hydroxy aldehyde; and contacting an alkaline additive with the amine salts to thereby cause dissociation of at least a portion of the amine salts.

36. The process according to claim 35, wherein the alkaline additive is added in the purification zone.

37. The process according to claim 35, wherein the alkaline additive is added upstream of the purification zone.

38. The process according to claim 37, wherein the alkaline additive is added downstream of the reaction zone.

39. The process according to claim 35, wherein the alkaline additive is added into the feed to the purification zone.

40. The process according to claim 35, wherein the alkaline additive is added in an amount that is less than 10 weight percent excess compared to the weight percent of the amine salts.

41. The process according to claim 35, wherein the Aldol condensation is carried out in a homogeneous reaction mixture.

42. The process according to claim 35, wherein the Aldol condensation reaction includes contacting formaldehyde and another aldehyde with the amine catalyst.

43. The process according to claim 42, wherein the another aldehyde comprises formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, or glutaraldehyde.

44. The process according to claim 42, wherein the another aldehyde is isobutyraldehyde.

45. The process according to claim 35, wherein the amine catalyst is triethylamine, tri-n-propylamine, tri-n-butylamine, trimethlyamine, or mixtures thereof.

46. The process according to claim 35, wherein the alkaline additive comprises a carbonate, a hydrogen carbonate, or a hydroxide of an alkali metal or alkaline earth metal.

47. The process according to claim 35, wherein the alkaline additive is $Na_2CO_3$, $K_2CO_3$, $CaCO_3$, $NaHCO_3$, $KHCO_3$, NaOH, KOH, $Ca(OH)_2$, or combinations thereof.

48. The process according to claim 35, wherein the hydroxy aldehyde comprises 3-hydroxypropanal, dimethylolethanal, trimethylolethanal (pentaerythrital), 3-hydroxybutanal (acetaldol), 3-hydroxy-2-ethylhexanal (butyl ldol), 3-hydroxy-2-methylpentanal (propyl ldol), 2-methylolpropanal, 2,2-dimethylolpropanal, 3-hydroxy-2-methylbutanal, 3-hydroxypentanal, 2-methylolbutanal, 2,2-dimethylolbutanal, or hydroxypivaldehyde.

49. The process according to claim 35, wherein the amine catalyst is trimethylamine, the alkaline additive is NaOH, and the hydroxy aldehyde is hydroxypivaldehyde.

50. The process according to claim 35, wherein the Aldol condensation reaction is carried out at a temperature in the range of from about 20° C. to about 150° C., a pressure in the range from about 5 psig to about 100 psig, and a total reaction time in the range of from about 30 minutes to about 2 hours.

51. The process according to claim 35, further comprising hydrogenating the purified product to form a polyol.

52. The process according to claim 51, wherein the polyol is neopentyl glycol.

53. The process according to claim 35, wherein the purifying is by distillation and produces an overhead stream, wherein the Aldol condensation reaction is carried out in a reactor, wherein at least a portion of said overhead stream is recycled back to the reactor, 54. The process according to claim 53, wherein the overhead stream comprises at least a portion of the amine catalyst.

55. The process according to claim 35, further comprising measuring the sodium and/or nitrogen content of the purified product, further comprising metering the amount of the alkaline additive contacted with the amine salt based on the measured sodium and/or nitrogen content of the purified product.

56. The process according to claim 35, wherein the process is a continuous process.

* * * * *